United States Patent

Fujimoto et al.

Patent Number: 5,216,009
Date of Patent: Jun. 1, 1993

[54] **METHOD FOR CONTROLLING *NILAPARVATA LUGENS***

[75] Inventors: Hiroaki Fujimoto, Osaka; Akira Shuto, Hyogo; Noriyasu Sakamoto, Hyogo; Hirosi Kisida, Hyogo; Noritada Matsuo, Hyogo; Kimitoshi Umeda, Osaka, all of Japan

[73] Assignee: Sumitomo Chemical Company, Limited, Osaka, Japan

[21] Appl. No.: 878,525

[22] Filed: May 5, 1992

[30] Foreign Application Priority Data

May 10, 1991 [JP] Japan ................. 3-105753
May 10, 1991 [JP] Japan ................. 3-135821

[51] Int. Cl.$^5$ .................. A01N 43/56; A01N 25/14
[52] U.S. Cl. ................... 514/406; 424/405; 424/421
[58] Field of Search .................. 424/405; 514/406

[56] References Cited

U.S. PATENT DOCUMENTS 4,943,586  7/1990  Bowers et al. ................. 514/406

FOREIGN PATENT DOCUMENTS 0376598  7/1990  European Pat. Off. .

OTHER PUBLICATIONS

European Search Report.

*Primary Examiner*—Thurman K. Page
*Assistant Examiner*—Neil Levy
*Attorney, Agent, or Firm*—Birch, Stewart, Kolasch & Birch

[57] ABSTRACT

A method for controlling insect pests which belong to Homoptera which comprises applying an insect pesticidally effective amount of the conpound having the formula:

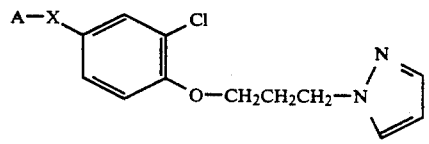

wherein A is a phenyl group, a 3-fluorophenyl group, a 3-chlorophenyl group and 3,5-difluorophenyl group; X is an oxygen atom or a methylene group, optionally together with an additive(s) and/or an inert carrier(s) to the said insect pests and/or the locus where the said insect pests propagage and/or cultivated plants to which the said insect pests do damage.

8 Claims, No Drawings

METHOD FOR CONTROLLING *NILAPARVATA LUGENS*

BACKGROUND OF THE INVENTION

1. Field of the Invention

The present invention relates to a method for controlling insect pests which belong to Homoptera.

2. Description of the Prior Art

It is described in U.S. Pat. No. 4,943,586 and European Patents Application No. 376,598 that certain pyrazole compounds are useful as insect pesticides.

It is very difficult to control insect pests which belong to Homoptera such as planthoppers, leafhoppers, aphids and whiteflies by reason of their specific ecological and physiological traits of character and furthermore very rapid development of drug-resistant system. So there are very severe damages in practical productions on Agriculture. However, there are few methods to effectively control such insect pests.

OBJECT OF THE INVENTION

As a result of the extensive study seeking method for effectively controlling such insect pests, it has been found that the following method exhibits a remarkable high controlling effect.

The main object of the present invention is to provide an improved method for controlling insect pests belonging to Homoptera.

This object as well as other objects and advantages of the present invention will become apparent to those skilled in the art from the following description.

SUMMARY OF THE INVENTION

The present invention relates to a method for controlling insect pests which belong to Homoptera which comprises applying an insect pesticidally effective amount of the compound having the formula:

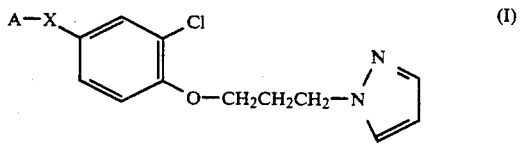

wherein A is a phenyl group, a 3-fluorophenyl group, a 3-chlorophenyl group and 3,5-difluorophenyl group; X is an oxygen atom or a methylene group, optionally together with an additive(s) and/or an inert carrier(s) to the said insect pests and/or the locus where the said insect pests propagate and/or cultivated plants to which the said insect pests do damage.

DETAILED DESCRIPTION OF THE INVENTION

The 4-substituted-2-chlorophenoxypropylpyrazole compounds (I) used as an active ingredient in the method of the present invention have an excellent juvenile hormone-like activity against insect pests which belong to Homoptera such as planthoppers, leafhoppers, aphids and whiteflies. They exhibit various strong actions such as metamorphosis inhibition, embryogenesis inhibition and sterilization and are thus efficacious as growth regulators, chemosterilants, ovicides or reproduction inhibitory agents on various insect pests which belong to Homoptera such as planthoppers, leafhoppers, aphids and whiteflies. They are also efficacious against insect pests having an increased resistance to commercial insecticides.

Among the 4-substituted-2-chlorophenoxypropylpyrazole compounds (I) as an active ingredient, preferred are those wherein X is an oxygen atom.

Examples of the insect pests which belong to Homoptera against which the method of the present invention exhibits controlling effects are as shown below.

Planthoppers such as brown rice planthopper (*Nilaparvata lugents*), small brown planthopper (*Laodelphax striatellus*) and whitebacked rice planthopper (*Sogatella furcifera*); leafhoppers such as green rice leafhoppers (*Nephotettix cincticeps, Nephotettix virescens, Nephotettix nigropictus* and *Nephotettix malayanus*), zig-zag rice leafhopper (*Recilia dorsalis*, grape leafhopper (*Arboridia apicalis*) and tea green leafhopper (*Empoasca onukii*); white flies such as greenhouse whitefly (*Trialeurodes vaporariorum*), sweet potato whitefly (*Bemisia tabaci*) and citrus spiny whitefly (*Aleurocanthus spiniferus*); aphids such as cotton aphid (*Aphis gossypii*), spiraea aphid (*Aphis citricola*), green peach aphid (*Myzus persicae*) and foxglove aphid (*Aulacorthum solani*).

Among the insect pests which belong to Homoptera as above exemplified, the method of the present invention is particularly effective in controlling those belong to genera such as Nilaparvata, Nephotetti, Trialeurodes, Bemisia and Aphis, and also exhibit a remarkable controlling effect on brown rice planthopper (*Nilaparvata lugens*), green rice leafhopper (*Nephotettix cincticeps*), greenhouse whitefly (*Trialeurodes vaporariorum*), sweet potato whitefly (*Bemisia tabaci*) and cotton aphid (*Aphis gossypii*).

In the method of the present invention, examples of cultivated plants are rice plants, vegetables, cottons, fruits and flowers, etc. Among the cultivated plants, the method of the present invention is most particularly effective in rice plants cultivated in a paddy field, to which the insect pests do most severe damage.

The method of the present invention may be used in mixtures of the 4-substituted-2-chlorophenoxypropylpyrazole compounds (I) as the active ingredient and other insecticides and/or acaricides to enhance or expand their insecticidal or pesticidal use.

Examples of the other insecticides and/or acaricide include organophosphorus compounds (e.g. fenitrothion (O,O-dimethyl O-(3-methyl-4-nitrophenyl)phosphorothioate), fenthion (O,O-dimethyl O-[3-methyl-4-(methylthio)phenyl]phosphorothioate), diazinon (O,O-diethyl-O-(2-isopropyl-6-methyl-pyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4-(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphoro-dithioate) and monocrotophos (dimethyl (E)-1-methyl-2-(methylcarbamoyl)vinyl phosphate), etc.); carbamate derivatives (e.g. BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-beta-alaninate), propoxur (2-isopropoxyphenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate), ethiofencarb (2-(ethylthiomethyl)phenyl methylcarbamate), aldicarb (2-methyl-2-(methylthio)propionaldehyde O-methylcarbamoyloxime) and Oxamyl (N,N-dimethyl-2-methylcarbamoyl-oxyimino-2-(methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), fenpropathrin ((RS)-alpha-cyano-3-phenoxybenzyl 2,2,3,3-tetramethylcyclopropanecarboxylate), cypermethrin ((RS)-alpha-cyano-3-phenoxybenzyl (1RS,3RS)-(1RS,3-RS)-3-(2,2-dichlorovinyl)-2,2-dimethylcyclopropanecarboxylate), permethrin (3-phenoxybenzyl (1RS,3RS)-(1RS,3-RS)-3-(2,2-dichlorovinyl)-2,2-dimethylcyclopropanecarboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alphacyano-m-phenoxybenzyl (1R,3R)-3-(2,2-dibromovinyl)-2-dimethylcyclopropanecarboxylate) and cycloprothrin ((RS)-alpha-cyano-3-phenoxybenzyl (RS)-2,2-dichloro-1-(4-ethoxyphenyl)cyclopropanecarboxylate), etc.); thiadiazine derivatives (e.g. buprofezin (2-tert-butylimino-3-isopropyl-5-phenyl-1,3,5-triadiazin-4-one), etc.); nitroimidazolidine derivatives (e.g. imidacloprid (1-(6-chloro-3-pyridylmethyl)-N-nitro-imidazolidin-2-ylideneamine), etc.); nereistoxin derivatives (e.g. cartap (S,S'-(2-dimethylaminotrimethylene) bis(thiocarbamate), thiocyclam (N,N-dimethyl-1,2,3-trithian-5-ylamine) and bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide) and gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phehyl]-3-(2,6-difluorobenzoyl)urea), teflubenzuron (1-(3,5-dichloro-2,4-difluorophenyl)-3-(2,6-difluorobenzoyl)urea) and flufenoxuron (1-[4-(2-chloro-4-trifluoromethylphenoxy)-2-fluorophenyl]-3-(2,6-difluorobenzoyl)urea, etc.); formamidine derivatives (e.g. amitraz (N,N'-[(methylimino)dimethylidyne]-di-2,4-xylidine) and chlordimeform (N'-(4-chloro-2-methylphenyl)-N,N-dimethylmethanimidamide), etc.).

On the practical use of the method of the present invention, the 4-substituted-2-chlorophenoxypropylpyrazole compound (I) as the active ingredient may be employed as such but are normally mixed with appropriate additives such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosals, heating smoking formulations (e.g. self-burning-type smoking formulations, chemical reaction-type smoking formulations, porous ceramic plate-type smoking formulations), ULV formulations, poison baits, etc.

The composition used in the method of the present invention contains generally the 4-substituted-2-chlorophenoxypropylpyrazole compound(s) (I) as the active ingredient in an amount of from about 0.001% to 95% by weight based on the composition.

Examples of the solid carrier usable for making the composition are fine powders or granules of clays (e.g. kaolin clay, diatomaceous earth, synthetic hydrated silica, bentonite, Fubasami clay, terra alba), talc, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitriles, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include freon gas, butane gas, LPG (liquefied petroleum gas), dimethyl ether, carbon dioxide, etc.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances (e.g. polyacrylic alcohol, polyvinylpyrrolidone, polyacrylic acid), etc. Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reaction-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazides, dinitrosopentamethylenetetramine, polystyrene and polyurethane, fillers such as natural fiber pieces and synthetic fiber pieces, etc. The base material for poison baits may contain feed components such as crop powders, essential vegetable oil, sugars and crystalline cellulose, antioxidants such as dibutylhydroxyrtolune and nordihydroguaiaretic acid, preservatives such as dehydroacetic acid, feeding error preventing agnets such as red paper powders, incentive flavors such as cheese flavor and onion flavor, etc.

Flowable concentrates (water-based suspension or emulsion formulations) are generally obtained by dispersing about 1 to 75 parts by weight of the 4-substituted-2-chlorophenoxypropylpyrazole compound (I) as the active ingredient finely and uniformly into water containing about 0.5 to 15 parts by weight of a dipersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anticorrosive agent, a stabilizing agent, a spreading agents, penetration auxiliaries, antifreezing agent, an antibacterial agent, an antimolding agent and the like. The use of an oil, into which the active ingredient is hardly soluble, in place of water affords oil-based suspension formulations. Examples of the protective colloids as above mentioned are gelatin, casein, gums, cellulose ethers, polyvinyl alcohol, etc. Examples of the compounds giving a thixotropic property are bentonite, aluminum magnesium silicate, xanthane gum, polyacrylic acid, etc.

The composition of the invention thus obtained may be used as such or after diluting with water. It may be also used in a mixture with any other active component or composition chosen from insecticides, nematoeides, acaricides, fungicides, bacteriocides, herbicides, plant growth regulators, synergistic agents, fertilizers, soil conditioners, animal feed, etc. Alternatively, the composition of the invention may be applied separately but simultaneously with said other active component or composition.

For the purpose of controlling insect pests in the agricultural field, the 4-substituted-2-chlorophenoxypropylpyrazole compound (I) as the active ingredient according to the method of the present invention may be applied to the insect pests or the locus where the insect pests propagate generally in an amount of about 0.001 g to 500 g, and preferably about 0.1 g to 500 g per 10 ares. when the 4-substituted-2-chlorophenoxypropylpyrazole compound (I) as the active ingredient is applied in a form of emulsifiable concentrate, wettable powder, flowable concentrate or the like after dilution with water, its concentration may be from about 0.0001 to 1000 ppm. Granules, dusts, etc. may be used as such, i.e. without water dilution. When the 4-substituted-2-chlorophenoxypropylpyrazole compound (I) as the active ingredient is used for household or public hygiene, it may be used in the form of emulsifiable concentrate, wettable powder, flowable concentrate or the like with water dilution, etc. In this case, the concentration of the active ingredient may be from about 0.0001 to 10,000 ppm. In case of oils, aerosol, fumigants, ULV formulations, poison baits, etc., they may be applied as such. However, the doses and concentrations may vary within broad ranges depending upon the composition, the application time, the place applied, the application method, the kind of insect pests, the condition of damage, etc. and may be increased or decreased, irrespective of the general ranges set forth above.

The 4-substituted-2-chlorophenoxypropylpyrazole compound (I) as the active ingredient in the method of the present invention can be produced by various processes, among which typical examples in the same manner as described in European Patents Application No. 376,598 are shown below.

The 4-substituted-2-chlorophenoxypropylpyrazole compound (I) is produced by reacting a compound having the formula:

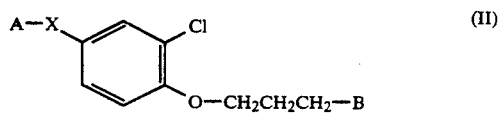

(II)

wherein B is a halogen atom, a methanesulfonyloxy group or a toluenesulfonyloxy group; R and X are each as defined above, with 1,2-pyrazole in the presence of a deoxidation agent. The reaction is ordinarily carried out with or without an inert solvent at a temperature of from about $-30°$ C. to about $200°$ C., preferably from about $0°$ C. to about $110°$ C. for from about 0.5 hour to about 30 hours.

The molar proportion of the compound (II) and 1,2-pyrazole to be used for the reaction is ordinary to be from 1:0.1 to 1:10, preferably to be from 1:0.8 to 1:1.2. Examples of the inert solvent are N,N-dimethylformamide, dimethylsulfoxide, tetrahydrofuran, toluene, 1,2-dimethylethane, dimethylacetoamide, etc. Examples of the deoxidation agent are alkali methals, alkali methal hydrides, alkali methal amides, alkali methal hydoxides, alkali methal carbonates and organic bases (e.g. 4-dimethylaminopyridine), etc.

When necessary or desired, an ammonium salt such as triethylbenzylbenzylammonium chloride and tetrabutylammonium bromide or an amine such as tris(3,6-dioxaheptyl) amine may be added to the reaction system as a catalyst. When the above catalyst is added to the reaction system, water or two layer mixtures of water and an organic solvent(s) may be used as the inert solvent.

After completion of the reaction, post-treatment may follow in a per se conventional manner such as extraction with an organic solvent and concentration. When necessary or desired, the product may further be purified by chromatography, distillation, recrystallization, etc.

Among the starting compounds in the above processes, the compound (II) wherein B is a halogen atom can be prepared from a phenol compound having the formula:

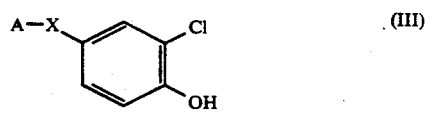

(III)

wherein A and X are each as defined above by the known method as described in Org. Synth., I, 435 (1932), etc. The compound (II) wherein B is a mathanesulfonyloxy group can be prepared from an alcohol compound having the formula:

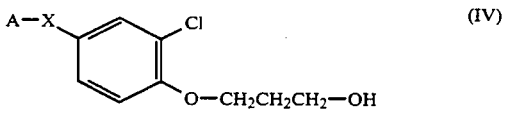

wherein A and X are each as defined above according to the method as described in U.S. Pat. No. 4,943,586.

Further, the compound (II) wherein B is a halogen atom can be also prepared from the alcohol compound (IV) according to the method as described in J. Amer. Chem. Soc., 68, 2513 (1946), J. Org. Chem., 14, 706 (1949), etc.

The phenol compound (III) can be prepared by reacting a corresponding non-chlorinated compound, i.e. a phenol compound, having the formula:

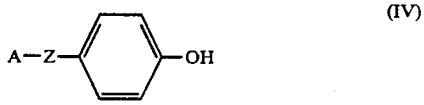

wherein A and Z are each as defined above, with a chlorinating agent by the known method as described in J. Amer. Chem., 73, 2723 (1951), J. Org. Chem., 39, 1160 (1974), etc.

The molar proportion of the phenol compound (IV) and the chlorinating agent is not limitative but it is ordinary to use the chlorinating agent in an amount equivalent to the phenol compound (IV) or somewhat in excess. Examples of the chlorinating agent are chlorine, tert-butyl hypochlorite, sulfuryl chloride, etc. If necessary and desired, the reaction can be carried out in the presence of an inert solvent. Examples of the solvent are dichloromethane, 1,2-dichloroethane, carbon tetrachloride, benzene, acetic acid, etc. The chlorinating agent itself may be available as a reaction medium when it is liquid. The reaction temperature is usually from about $-80°$ C. to the refluxing temperature of the reaction system, preferably from about $-20°$ C. to the refluxing temperature of the reaction system.

After completion of the reaction, post-treatment may follow in a per se conventional manner such as extraction with an organic solvent and concentration. When necessary or desired, the product may further be purified by chromatography, distillation, recrystallization, etc.

The phenol compound (IV) and 1,2-pyrazole are available on the commercial market or can be readily produced from appropriate commercial products by conventional method.

Practical and presently preferred embodiments of the invention will be hereinafter explained in more detail referring to Formulation Examples, Test Examples and Production Examples of the 4-substituted-2-chlorophenoxypropylpyrazole compound (I) as the active ingredient.

These examples, however, should not be construed to be limitative.

In the following Production Examples, % is by weight unless otherwise indicated.

PRODUCTION EXAMPLE (OF THE ACTIVE INGREDIENT) 1

Production of the Compound No. 3

To a mixture of 5 ml of anhydrous N,N-dimethylformamide and 52 mg of sodium hydride (60% oily suspension), there was added 84 mg of pyrazole with stirring. After 30 minutes, a solution of 463 mg of 3-[2-chloro-4-(3-chlorophenoxy)phenoxy]propylbromide in 5 ml of anhydrous N,N-dimethylformamide was added thereto at room temperature, followed by stirring at the same temperature for 5 hours.

The reaction mixture was diluted with 50 ml of ethyl acetate. The diluted mixture was washed twice with 30 ml of a saturated aqueous solution of ammonium chloride, dried over anhydrous magnesium sulfate and concentrated under reduced pressure. The residue was subjected to silica gel chromatography to give 340 mg of 1-[3-{2-chloro-4-(3-chlorophenoxy)phenoxy} propyl]pyrazole as a colorless oily substance. Yield: 76%, $n^{23.9}_D$:1.5879.

PRODUCTION EXAMPLE (OF THE ACTIVE INGREDIENT) 2

Production of Compound No. 4

To a mixture of 5 ml of anhydrous N,N-dimethylformamide and 42 mg of sodium hydride (60% oily suspension), there was added 79 mg of pyrazole with stirring. After 30 minutes, a solution of 400 mg of 3-[2-chloro-4-(3,5-difluorophenoxy)phenoxy]propylbromide in 5 ml of anhydrous N,N-dimethylformamide was added thereto at room temperature, followed by stirring at the same temperature for 5 hours.

The reaction mixture was diluted with 50 ml of ethyl acetate. The diluted mixture was washed twice with a saturated aqueous solution of ammonium chloride, dried over anhydrous magnesium sulfate and concentrated under reduced pressure. The residue was subjected to silica gel chromatography to give 317 mg of 1-[3-{2-chloro-4-(3,5-difluorophenoxy)phenoxy} propyl]pyrazole as a colorless oily substance. Yield: 82%, $n^{24.1}_D$:1.5535.

PRODUCTION EXAMPLE (OF THE ACTIVE INGREDIENT) 3

Production of Compound No. 7

To a mixture of 5 ml of anhydrous N,N-dimethylformamide and 34 mg of sodium hydride (60% oily suspension), there was added 57 mg of pyrazole with stirring. After 30 minutes, a solution of 300 mg of 3-[2-chloro-4-(3-chlorobenzyl)phenoxy]propylbromide in 5 ml of anhydrous N,N-dimethylsulfoxide was added thereto at room temperature, followed by stirring at the same temperature for 5 hours.

The reaction mixture was diluted with 50 ml of ethyl acetate. The diluted mixture was washed twice with a saturated aqueous solution of ammonium chloride, dried over anhydrous magnesium sulfate and concentrated under reduced pressure. The residue was subjected to silica gel chromatography to give 197 mg of 1-[3-{2-chloro-4-(3-chlorobenzyl)phenoxy}propyl]-pyrazole as a colorless oily substance. Yield: 68%, m.p.: 52.5° C. Some examples of the 4-substituted-2-chlorophenoxypropylpyrazole compound (I) as the active ingredient were produced in the same manner as described above and shown in Table 1.

TABLE 1

| Compound No. | Chemical structure | Physical constant |
|---|---|---|
| 1 | phenyl—O—(2-Cl-phenyl)—O—CH$_2$CH$_2$CH$_2$—N(pyrazole) | $n_D^{22.9}$ 1.5855 |
| 2 | (4-F-phenyl)—O—(2-Cl-phenyl)—O—CH$_2$CH$_2$CH$_2$—N(pyrazole) | $n_D^{24.1}$ 1.5729 |
| 3 | (3-Cl-phenyl)—O—(2-Cl-phenyl)—O—CH$_2$CH$_2$CH$_2$—N(pyrazole) | $n_D^{23.9}$ 1.5879 |
| 4 | (3,5-diF-phenyl)—O—(2-Cl-phenyl)—O—CH$_2$CH$_2$CH$_2$—N(pyrazole) | $n_D^{24.2}$ 1.5535 |
| 5 | phenyl—CH$_2$—(2-Cl-phenyl)—O—CH$_2$CH$_2$CH$_2$—N(pyrazole) | $n_D^{24.2}$ 1.5842 |
| 6 | (3-F-phenyl)—CH$_2$—(2-Cl-phenyl)—O—CH$_2$CH$_2$CH$_2$—N(pyrazole) | m.p. 45.1° C. |
| 7 | (3-Cl-phenyl)—CH$_2$—(2-Cl-phenyl)—O—CH$_2$CH$_2$CH$_2$—N(pyrazole) | m.p. 52.5° C. |
| 8 | (3,5-diF-phenyl)—CH$_2$—(2-Cl-phenyl)—O—CH$_2$CH$_2$CH$_2$—N(pyrazole) | $n_D^{22.7}$ 1.5817 |

In Formulation Examples as set forth below, parts and % are all by weight. The compound numbers correspond to those as shown in Table 1.

FORMULATION EXAMPLE 1

Emulsifiable Concentrate

To a solution of 10 parts of each of Compounds Nos. 1 to 8 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10%.

FORMULATION EXAMPLE 2

Wettable Powder

Twenty parts of each of Compounds Nos. 1 to 8 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20%.

FORMULATION EXAMPLE 3

Granules

Five parts of sodium dodecylbenzenesulfonate, 30 parts of bentonite and 60 parts of clay are added to 5 parts of each of Compound Nos. 1, 2, 3, 4, 5 and 8, and the resultant mixture is pulverized and kneaded with a suitable amount of water. The mixture is granulated in a granulator and air-dried to give granules containing the active ingredient in 5%.

FORMULATION EXAMPLE 4

Granules

Five parts of fine powders of synthetic hydrated silica, 5 parts of sodium dodecylbenzenesulfonate, 30 parts of bentonite and 55 parts of clay are added to 5 part of each of Compound Nos. 6 and 7, and the resultant mixture is pulverized and kneaded with a suitable amount of water. The mixture is granulated in a granulator and air-dried to give granules containing the active ingredient in 5%.

FORMULATION EXAMPLE 5

Dusts

To a mixture of 1 part of fine powders of synthetic hydrated silica, 1 part of an aggregating agent ("Driless B" manufactured by Sankyo Co., Ltd.) and 7.7 parts of clay, 0.3 part of each of Compound Nos. 1, 2, 3, 4, 5 and 8 is added, and the resultant mixture is well pestled in a mortar and further stirred in a mixer. To the thus obtained mixture, there are added 90 parts of cut clay, followed by mixing to give dusts containing the active ingredient in 0.3.

FORMULATION EXAMPLE 6

Dusts

A mixture of 0.3 part of each of Compound Nos. 6 and 7 and 0.03 part of fine powders of synthetic hydrated silica is stirred well in a mixer and pulverized by the aid of a centrifugal pulverizer. To the resultant mixture, 0.97 part of fine powders of synthetic hydrated silica, 1 part of "Driless B" and 7.7 parts of clay are added, and the resulting mixture is pestled in a mortar and stirred in a mixer. Ninety parts of cut clay are added thereto, and further mixing is effected in a sack to give dusts containing the active ingredient in 0.3%.

FORMULATION EXAMPLE 7

Dusts

A mixture of 0.3 part of each of Compound Nos. 1, 2, 3, 4, 5 and 8, 2 parts of fenitrothion (O,O-dimethyl O-(3-methyl-4-nitrophenyl)phosphorothioate as an organophosphorus insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

FORMULATION EXAMPLE 8

Dusts

A mixture of 0.3 part of each of Compound Nos. 6 and 7 and 0.03 part of fine powders of synthetic hydrated silica is stirred in a mixer and pulverized by a centrifugal pulverizer. After addition of 2 parts of fenitrothion, 2.97 parts of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

FORMULATION EXAMPLE 9

Dusts

A mixture of 0.3 part of each of Compound Nos. 1, 2, 3, 4, 5 and 8, 2 parts of BPMC (O-sec-butylphenyl N-methylcarbamate) as a carbamate insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

FORMULATION EXAMPLE 10

Dusts

A mixture of 0.3 part of each of Compound Nos. 6, and 7 and 0.03 part of fine powders of synthetic hydrated silica is stirred in a mixer and pulverized by a centrifugal pulverizer. After addition of 2 part of BPMC, 2.97 part of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

FORMULATION EXAMPLE 11

Dusts

To a solution of 1 part of each of Compound Nos. 1 to 8 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give dusts containing the active ingredient in 1%.

FORMULATION EXAMPLE 12

Flowable Concentrate

To 40 parts of an aqueous solution containing 2 parts of polyvinyl aocohol, 10 parts of each of Compound Nos. 1, 2, 3, 4, 5 and 8 are added, and the resultant mixture is stirred in a mixer. To the obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10%.

FORMULATION EXAMPLE 13

Flowable Concentrate

To 28.5 parts of an aqueous solution containing 2 parts of polyvinyl alcohol, 20 parts of each of Compound Nos. 6 and 7 and 1.5 parts of sorbitan trioleate are added, and the resultant mixture is finely pulverized by the aid a sand grinder to give particles of less than 3 microns in average particle size. To the resultant mixture, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 20%.

FORMULATION EXAMPLE 14

Oil Spray

Into a mixture of 5 parts of xylene and 5 parts of trichloroethane, 0.1 part of each of Compound Nos. 1 to 8 is dissolved, and the resultant solution is mixed with 89.9 parts of deodorized kerosene to give an oil spray containing the active ingredient in 0.1%.

FORMULATION EXAMPLE 15

Oil-Based Aerosol

A solution of 0.1 part of each of Compound Nos. 1 to 8, 0.2 part of tetramethrin (2,2-dimethyl-3-(2-methyl-1-propenyl)cyclopropanecarboxylic acid (1,2,3,4,5,7-hexahydro-1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under compression to give an oil-based aerosol.

FORMULATION EXAMPLE 16

Water-Based Aerosol

A solution of 0.2 part of each of Compound Nos. 1 to 8, 0.2 part of d-allethrin (2,2-dimethyl-3-(2-methyl-1-propenyl)cyclopropanecarboxylic acid 2-methyl-4-oxo-3-(2-propenyl)-2-cyclopenten-2-yl ester), 0.2 part of d-phenothrin, 5 parts of xylene, 3.4 parts of deodorized kerosene and 1 part of an emulsifier ("ATMOS 300" ®, Atlas Chemical Co., Ltd.) in 50 parts of destilled water is filled in an aerosol container. After provision of a valve, 40 parts of a propellant (liquefied petroleum gas) is filled through the valve under compression to give a water-based aerosol.

FORMULATION EXAMPLE 17

Fumigant

Each of Compound Nos. 1 to 8 (100 mg) is dissolved in an appropriate amount of acetone, and the resultant solution is impregnated with a porous ceramic plate (4.0×4.0×1.2 cm) to give a fumigant.

The following Test Examples show some of test results which support the controlling effect of the 4-substituted-2-chlorophenoxypropylpyrazole compounds (I) as the active ingredient on insect pests. The compound numbers correspond to those as shown in Table 1. The compounds used for comparison are as follows:

TABLE 2

| Compound symbol | Chemical structure | Remarks |
| --- | --- | --- |
| A | [phenyl-O-phenyl-O-CH₂-CH₂-N-pyrazole] | Compound disclosed in U.S. Pat. No. 4,943,586 |
| B | [Cl-phenyl-O-phenyl-O-CH₂-CH₂-N-pyrazole] | Compound disclosed in U.S. Pat. No. 4,943,586 |
| C | [phenyl-O-(F-phenyl)-O-CH₂-CH₂-N-pyrazole] | Compound disclosed in U.S. Pat. No. 4,943,586 |
| D | [phenyl-O-phenyl-O-CH₂-CH₂-CH₂-N-pyrazole] | Compound disclosed in European EP-A-376,598 |
| E | [Cl-phenyl-O-phenyl-O-CH₂-CH₂-CH₂-N-pyrazole] | Compound disclosed in European EP-A-376,598 |

TEST EXAMPLE 1

Metamorphosis Inhibitory Activity Against Brown Rice Planthopper Nymphs

An emulsifiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphs of brown rice planthopper (*Nilaparvata lugens*). After 10 days, the number of normal adults was counted to obtain an emergence inhibitory rate. The results are shown in Table 4.

TABLE 3

| Compound No. | Concentration (ppm) | Inhibitory rate (%) |
|---|---|---|
| 1 | 5 | 100 |
|   | 0.5 | 100 |
| 2 | 5 | 100 |
|   | 0.5 | 100 |
|   | 0.05 | 100 |
| 3 | 5 | 100 |
|   | 0.5 | 100 |
|   | 0.05 | 100 |
| 4 | 5 | 100 |
|   | 0.5 | 100 |
|   | 0.05 | 100 |
| 5 | 5 | 100 |
|   | 0.5 | 100 |
|   | 0.05 | 100 |
| 6 | 5 | 100 |
|   | 0.5 | 100 |
|   | 0.05 | 100 |
| 7 | 5 | 100 |
|   | 0.5 | 100 |
|   | 0.05 | 100 |
| 8 | 5 | 100 |
|   | 0.5 | 100 |
| A | 50 | 0 |
|   | 5 | 0 |
| B | 50 | 0 |
|   | 5 | 35 |
| C | 50 | 90 |
|   | 5 | 29 |
| D | 5 | 30 |
|   | 0.5 | 10 |
| E | 5 | 13 |
|   | 0.5 | 8 |

TEST EXAMPLE 2

Reproduction Inhibitory Activity Against Green Rice Leafhopper

An emulsifiable concentrate prepared according to Formulation Example 1 was diluted with water to make a predetermined concentration. The dilution was sprayed onto rice plants, (about 20 cm in height) cultivated in plastic polts (1/5000 are in width) at a rate of 40 ml/2 pots on a turning table. After air-drying, the pots were covered with wire cages, and each 10 male and female adults of green rice leafhopper (Nephotettix cincticeps) were released in each of the cages. After 3 weeks, the number of nymphs was counted to obtain a reproduction inhibitory rate. The results are shown in Table 4.

TABLE 4

| Compound No. | Concentration (ppm) | Inhibitory rate (%) |
|---|---|---|
| 1 | 200 | 100 |
| 2 | 200 | 100 |
| 3 | 200 | 100 |
| 4 | 200 | 100 |
| 5 | 200 | 100 |
| 6 | 200 | 100 |
| 7 | 200 | 100 |
| 8 | 200 | 100 |

TEST EXAMPLE 3

Ovicidal Activity Against Greenhouse Whitefly

An emulsifiable concentrate prepared according to Formulation Example 1 was diluted with water to make a predetermined concentration. Into the dilution, leaf discs of kidney bean with eggs laid during from 48 hours to 72 hours by aduls of greehouse whitefly (Trialeurodes vaporariorum) were dipped for 10 seconds. After 7 days, the number of hatchlings was counted to obtain an ovicidal rate. The results are shown in Table 5.

TABLE 5

| Compound No. | Concentration (ppm) | Ovicidal rate (%) |
|---|---|---|
| 1 | 10 | 100 |
| 2 | 10 | 100 |
| 3 | 10 | 100 |
| 4 | 10 | 100 |
| 5 | 10 | 100 |
| 6 | 10 | 100 |
| 7 | 10 | 100 |
| 8 | 10 | 100 |

TEST EXAMPLE 4

Reproduction Inhibitory Activity Against Cotton Aphids

An emulsifiable concentrate prepared according to Formulation Example 1 was diluted with water to make a predetermined concentration. The dilution was sprayed onto potted cotton plants (in a stage of 8-9 days after sowing) infested with 1st instar nymphs of cotton aphids (Aphis gossypii) at a rate of 30 ml/2 pots on a turning table. Before spraying and one week after spraying, the number of nymphs and aduts was counted, and a reproduction inhibitory index was expressed by the following equation:

$$\text{Reproduction inhibitory index} = \frac{\text{Number of individuals one week after spraying per 2 pots}}{\text{Number of individuals before spraying per 2 pots}}$$

wherein the judgement of activity is based on the following standard:

A: less than 1 (excellent effect)
B: from 1 to 3 (slight effect)
C: more than 3 (little effect)
D: same as in the untreated pots (no effect)

The results are shown in Table 7.

TABLE 7

| Compound No. | Concentration (ppm) | Inhibitory rate |
|---|---|---|
| 1 | 100 | A |
| 3 | 100 | A |
| 4 | 100 | A |
| 6 | 100 | A |

What is claimed is:

1. A method for controlling *Nilaparvata lugens* which comprises applying 1-[3-(2-chloro-4-phenoxy-phenoxy)propyl]pyrazole at an amount of from 0.001 g to 500 g per 10 ares to the said insect pests and/or rice plants.

2. A method for controlling *Nilaparvata lugens* which comprises applying 1-[3-{2-chloro-4-(3-fluorophenoxy)-phenoxy}propyl]pyrazole at an amount of from 0.001 g to 500 g per 10 ares to the said insect pests and/or rice plants.

3. A method for controlling *Nilaparvata lugens* which comprises applying 1-[3-{2-chloro-4-(3-chlorophenoxy)-phenoxy}propyl]pyrazole at an amount of from 0.001 g to 500 g per 10 ares to the said insect pests and/or rice plants.

4. A method for controlling *Nilaparvata lugens* which comprises applying 1-[3-{2-chloro-4-(3,5-difluorophenoxy)phenoxy}propyl]pyrazole at an amount of from 0.001 g to 500 g per areas to the said insect pests and/or rice plants.

5. A method for controlling *Nilaparvata lugens* which comprises applying 1-[3-(2-chloro-4-benzylphenoxy)propyl]pyrazole at an amount of from 0.001 g to 500 g per 10 ares to the said insect pests and/or rice plants.

6. A method for controlling *Nilaparvata lugens* which comprises applying 1-[3-{2-chloro-4-(3-fluorobenzyl)phenoxy}propyl]pyrazole at an amount of from 0.001 g to 500 g per 10 ares to the said insect pests and/or rice plants.

7. A method for controlling *Nilaparvata lugens* which comprises applying 1-[3-{2-chloro-4-(3-chlorobenzyl)phenoxy}propyl]pyrazole at an amount of from 0.001 g to 500 g per areas to the said insect pests and/or rice plants.

8. A method for controlling *Nilaparvata lugens* which comprises applying 1-[3-{2-chloro-4-(3,5-difluorobenzyl)phenoxyl}propyl]pyrazole at an amount of from 0.001 g to 500 g per 10 ares to the said insect pests and/or rice plants.

* * * * *